(12) United States Patent
Chen et al.

(10) Patent No.: US 10,271,741 B2
(45) Date of Patent: Apr. 30, 2019

(54) BIOMETRIC SCALE

(71) Applicants: Huami Inc., Mountain View, CA (US); Anhui Huami Information Technology Co.,Ltd., Hefei (CN)

(72) Inventors: Ting Chen, Mountain View, CA (US); Fei Wang, Mountain View, CA (US); Yajun Zhao, Hefei (CN); Jixiang Su, Hefei (CN)

(73) Assignees: Huami Inc., Mountain View, CA (US); Anhui Huami Information Technology Co., Ltd., Hefei (CN)

( * ) Notice: Subject to any disclaimer, the term of this patent is extended or adjusted under 35 U.S.C. 154(b) by 245 days.

(21) Appl. No.: 15/070,737

(22) Filed: Mar. 15, 2016

(65) Prior Publication Data

US 2017/0071478 A1 Mar. 16, 2017

Related U.S. Application Data

(63) Continuation-in-part of application No. 14/854,569, filed on Sep. 15, 2015.

(51) Int. Cl.
*A61B 5/00* (2006.01)
*A61B 5/0205* (2006.01)
(Continued)

(52) U.S. Cl.
CPC ............ *A61B 5/0205* (2013.01); *A61B 5/044* (2013.01); *A61B 5/0408* (2013.01); *A61B 5/117* (2013.01);
(Continued)

(58) Field of Classification Search
USPC ...................................... 600/508–509; 702/19
See application file for complete search history.

(56) References Cited

U.S. PATENT DOCUMENTS

| | | | |
|---|---|---|---|
| 4,803,625 A | 2/1989 | Fu et al. | |
| 5,620,003 A | 4/1997 | Sepponen | |

(Continued)

FOREIGN PATENT DOCUMENTS

| | | |
|---|---|---|
| JP | 2006255099 A | 9/2006 |
| WO | 2009027556 A2 | 3/2009 |

OTHER PUBLICATIONS

Qardiobase Wireless Smart Scale Weight Management Redefined; https://www.getqardio.com/qardiobase-smart-scale-iphone-android/; Mar. 15, 2016; 8 pages.

(Continued)

*Primary Examiner* — Nicole F Lavert
*Assistant Examiner* — Nicole F Johnson
(74) *Attorney, Agent, or Firm* — Young Basile Hanlon & MacFarlane, P.C.

(57) ABSTRACT

A method for configuring a monitoring component for a user includes receiving an electrocardiograph (ECG) signal from an ECG component, receiving a weight signal from a scale component, and combining features extracted from the ECG signal and the weight signal to generate a current biometric signal. Responsive to the current biometric signal matching a historical biometric signal, the method includes obtaining a user profile and determining a health status for association with the user profile by classifying the current biometric signal using disease models and fitness models.

21 Claims, 5 Drawing Sheets

(51) Int. Cl.
*A61B 5/044* (2006.01)
*A61B 5/0408* (2006.01)
*G01G 19/50* (2006.01)
*A61B 5/117* (2016.01)

(52) U.S. Cl.
CPC .......... *A61B 5/6887* (2013.01); *A61B 5/7267* (2013.01); *A61B 5/7475* (2013.01); *G01G 19/50* (2013.01); *A61B 5/726* (2013.01)

(56) References Cited

U.S. PATENT DOCUMENTS

| | | | |
|---|---|---|---|
| 7,283,870 | B2 | 10/2007 | Kaiser et al. |
| 7,689,833 | B2 | 3/2010 | Lange |
| 9,173,577 | B2 | 11/2015 | Yuen et al. |
| 2002/0151803 | A1 | 10/2002 | Kouou |
| 2007/0021979 | A1 | 1/2007 | Cosentino et al. |
| 2008/0221404 | A1 | 9/2008 | Tso |
| 2013/0157244 | A1* | 6/2013 | Eger .......... G09B 7/00 434/350 |
| 2013/0297219 | A1* | 11/2013 | Bangera .......... G06F 19/345 702/19 |
| 2015/0338265 | A1 | 11/2015 | Carreel et al. |

OTHER PUBLICATIONS

Withings Smart Body Analyzer; http://www.withings.com/us/en/products/smart-body-analyzer; Mar. 15, 2016; 13 pages.
Omron Body Composition Monitor and Scale With Seven Fitness Indicators; https://omronhealthcare.com/products/body-composition-monitor-scale-seven-indicators-hbf514c/; Mar. 15, 2016; 4 pages.
Ihealth Core Wireless Body Composition Scale; https://ihealthlabs.com/wireless-scales/ihealth-core/; Feb. 26, 2016; 3 pages.
RD 901 Tanita Innerscan Dual Frequency Body Composition Monitor With Bluetooth 4.0 and Iphone App; http://tanita.eu/static/rd901.html; Feb. 26, 2016; 6 pages.
Larburu et al. "Comparative study of algorithms for Atrial Fibrillation Detection," Computing in Cardiology, 2011; 4 pages.

* cited by examiner

BIOMETRIC SCALE

CROSS-REFERENCE TO RELATED APPLICATION(S)

This application is a continuation-in-part of U.S. patent application Ser. No. 14/854,569 titled "Wearable Biometric Measurement Device," filed Sep. 15, 2015, and incorporated herein by reference in its entirety.

TECHNICAL FIELD

This disclosure relates to a monitoring component using both weight and other biometric signals to identify a user and track biometric information associated with the user.

BACKGROUND

Biometric characteristics have been used to identify unique users for various purposes, including access control. These characteristics conventionally include fingerprints, DNA, retinal maps, facial recognition, etc., the likes of which are secure but expensive identification solutions.

Device users involved in fitness programs or at risk for various diseases may wish not only to be easily identified but also to monitor both weight data and other biometric data, for example, to identify fitness conditions, risk factors, or disease diagnoses. Means currently available to capture weight data and other biometric data are present in separate devices, are overly cumbersome in terms of identification methods, connections, wires, etc., or can offer only a single source for biometric data.

SUMMARY

Disclosed herein is method for configuring a monitoring component for a user. The method includes receiving an electrocardiograph (ECG) signal from an ECG component, receiving a weight signal from a scale component, and combining features extracted from the ECG signal and the weight signal to generate a current biometric signal. Responsive to the current biometric signal matching a historical biometric signal, the method further includes obtaining a user profile and determining a health status for association with the user profile by classifying the current biometric signal using disease models and fitness models.

Also disclosed herein is a system including an electrocardiogram (ECG) component comprising a first, second, and third electrode wherein a first ECG lead configured to generate a first ECG signal is formed upon user contact with the first and second electrodes and wherein second and third ECG leads configured to generate second and third ECG signals are formed upon user contact with the first, second, and third electrodes. The system further includes a scale component comprising a platform configured to support the user and a weight sensor in communication with the platform and configured to generate a weight signal based on user presence on the platform.

The system also includes a monitoring component comprising a non-transitory memory and a processor configured to execute instructions stored in the non-transitory memory to receive the first, second, or third ECG signal from the ECG component, receive the weight signal from the scale component, and combine features extracted from the first, second, or third ECG signal and the weight signal to generate a current biometric signal. Responsive to the current biometric signal matching a historical biometric signal, the monitoring component will obtain a user profile and determine a health status for association with the user profile by classifying the current biometric signal using disease models and fitness models.

Also disclosed herein is a monitoring component including a non-transitory memory and a processor configured to execute instructions stored in the non-transitory memory to receive an electrocardiograph (ECG) signal from an ECG component in contact with a user, receive a weight signal from a scale component in contact with the user, and combine features extracted from the ECG signal and the weight signal to generate a current biometric signal. Responsive to the current biometric signal matching a historical biometric signal, the processor is further configured to obtain a user profile and determine a health status for association with the user profile by classifying the current biometric signal using disease models and fitness models.

Details of these implementations, modifications of these implementations, and additional implementations are described below.

BRIEF DESCRIPTION OF THE DRAWINGS

The disclosure is best understood from the following detailed description when read in conjunction with the accompanying drawings. It is emphasized that, according to common practice, the various features of the drawings are not to scale. On the contrary, the dimensions of the various features are arbitrarily expanded or reduced for clarity.

DETAILED DESCRIPTION

A monitoring system in the form of a biometric scale captures ECG signals using electrodes and weight signals using a weight sensor for the purposes of both identifying a user and providing a health status to the user. Identification and health status are determined by comparing an analyzed version of the ECG and weight signals in the form of current biometric data to disease models, fitness models, and historical biometric data associated with a user profile. The analysis of the biometric data can occur either directly at the biometric scale or remotely, for example, using a mobile device or a wearable device.

Figure 1:
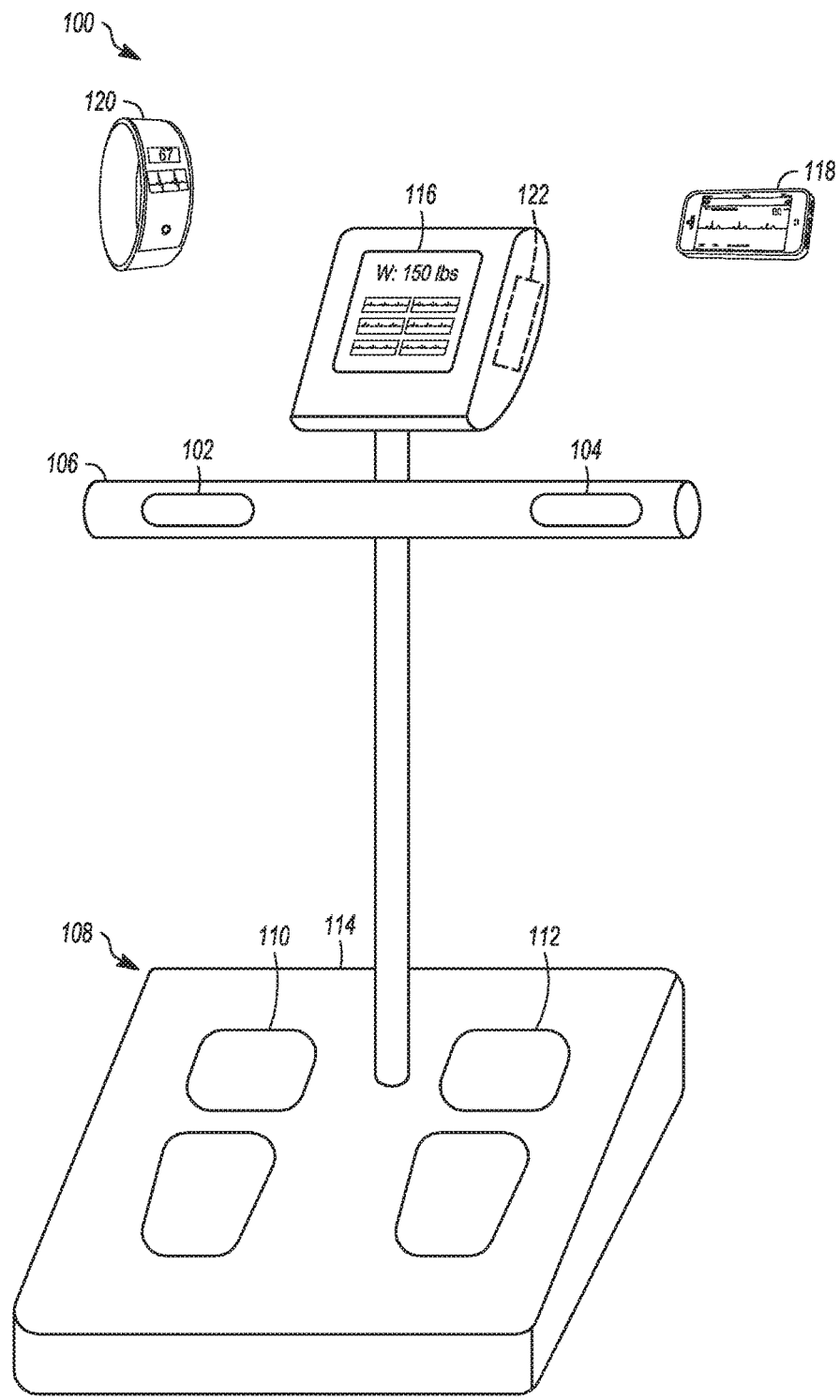
FIG. 1 shows a schematic illustration of a monitoring system.

FIG. 1 shows a schematic illustration of a monitoring system 100. The monitoring system 100 collects biometric data using contact-based communication with a user's hands and feet for purposes of identifying the user and providing a health status to the user.

The monitoring system 100 includes an ECG component that can be selectively trained to identify specific ECG signals from the user, for example, in order to identify stress levels or detect or diagnose specific diseases or disease risk factors. To that end, the ECG component includes first and second electrodes 102 and 104 disposed on a handle 106 that are configured to measure various aspects of the user's heart function and related biometrics through a touch input or contact with the user's palms and/or fingers when the user grabs the handle 106. The first and second electrodes 102 and 104 are configured to identify electrical heart activity by measuring the user's pulse and transmitting the ECG signal for subsequent encoding and processing. That is, upon the user contacting both the first electrode 102 and the second electrode 104, for example, with the palms or fingers of opposite hands, an ECG lead is formed, allowing the monitoring system 100 to measure the user's heart activity. The first and second electrodes 102 and 104 can additionally be configured to collect fingerprints or palm prints from the user for identification purposes.

The monitoring system 100 also includes a base 108 with another ECG component comprising third and, optionally, fourth electrodes 110 and 112 configured to measure various aspects of the user's heart function and related biometrics through contact with the user's feet when the user stands on the base 108 without socks or shoes. When the user contacts both the third electrode 110 of the base 108 while at the same time contacting the first electrode 102 and the second electrodes 104 on the handle 106, a total of three ECG leads are formed, allowing detection or diagnoses of additional diseases or disease risk factors. For example, the second of the ECG leads is based on voltage between the electrode 104, generally in contact with the user's right fingers or palm, and the electrode 110, generally in contact with the user's left foot. The third ECG lead is based on voltage between electrode 102, generally in contact with the user's left fingers or palm, and the electrode 110, again, generally in contact with the user's left foot.

The base 108 can also include a scale component. The scale component can include a platform 114 configured to support the user and a weight sensor (not shown) in communication with the platform 114 and configured to generate a weight signal based on user presence on the platform 114. The weight sensor can be a generally known device comprising load cells, pressure transducers, linear variable differential transformers, capacitance coupled sensors, or strain gages configured to convert the user's physical weight into weight data that is representative of the user's weight.

Though the various electrodes 102, 104, 110, 112 and the weight sensor described above are designed to capture and generate ECG data, weight data, and optionally, fingerprint and palm print data, four types of biometric data, further signal detection components can be included within the monitoring system 100. For example, the monitoring system 100 can include a thermometer component comprising a temperature sensor (not shown) configured to measure the user's body temperature or a pulse oximeter (not shown) configured to measure the user's blood oxygen level. The various types of biometric data that can be captured and processed by the monitoring system 100 can be useful, for example, in establishing identity of the user and tracking a health status or overall fitness level for the user as described further below.

The monitoring system 100 can also include a display 116 configured to visually represent collected biometric data. In one implementation, the display 116 can be a single output screen for visually representing all collected biometric data. For example, and as shown in FIG. 1, the display 116 includes a single output screen that visually represents both the user's weight in numerical form (e.g., W: 150 lbs.) and the user's heart activity from the first, second, and third ECG leads in graphical form. The information outputted to the display 116 may be updated as additional biometric data is processed by the monitoring system 100.

In another implementation, the display 116 may be a plurality of output screens with each output screen visually representing a unique type of collected biometric data. Further, the biometric data captured by the monitoring system 100 can be sent to separate devices for processing or display. For example, in another implementation, weight data and ECG data can be outputted to a user on a display included within a mobile device such as a smart phone 118. In yet another implementation, weight data and ECG data can be outputted to a user on a display included within a wearable device such as a bracelet 120. Though a mobile device and a wearable device are given as examples, other devices can also be in communication with the monitoring system 100 to process or display information associated with the biometric data collected using the various electrodes 102, 104, 110, 112 and weight sensors.

The monitoring system 100 can also include a monitoring component in the form of a computing device 122 configured to process and/or transmit biometric data collected by the ECG component and the scale component of the monitoring system 100. Processing capabilities of the computing device 122 are described further below. The computing device 122 can also be designed to transmit biometric data to separate devices, such as the smart phone 118 or the bracelet 120 for processing and/or display. The computing device 122 can also be designed to transmit biometric data to a medical examiner for review, diagnosis of disease, or other treatment purposes. The computing device 122 can also be designed to transmit biometric data to a database or other related system for storage, such as for later review or comparison in the form of historical biometric data. In one implementation, the computing device 122 includes a Bluetooth transmitter; however, the computing device 122 can communicate with other suitable wireless communication systems, including, without limitation, an ultrasound transmitter.

Figure 2:
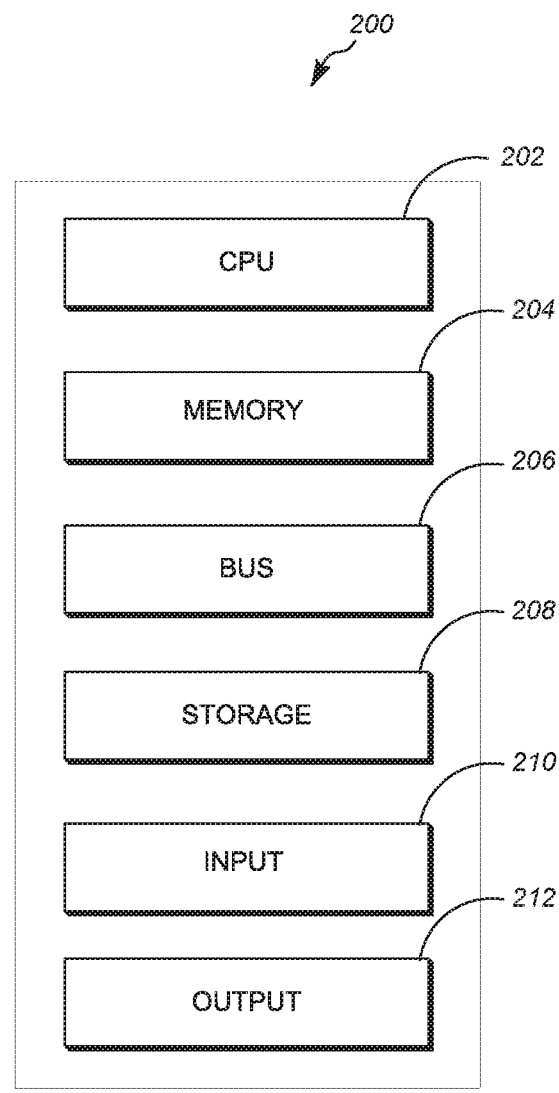
FIG. 2 is a block diagram of a hardware configuration for the monitoring system of FIG. 1.

FIG. 2 is a block diagram of a hardware configuration 200 for the monitoring system 100 of FIG. 1. The hardware configuration 200 can include at least one processor such as central processing unit (CPU) 202. Alternatively, CPU 202 can be any other type of device, or multiple devices, capable of manipulating or processing information now-existing or hereafter developed. Although the examples herein can be practiced with a single processor as shown, advantages in speed and efficiency can be achieved using more than one processor.

The hardware configuration 200 can include a memory 204 such as a random access memory device (RAM), a read-only memory device (ROM), or any other suitable type of storage device that stores code and data that can be accessed by the CPU 202 using a bus 206. The code can include an operating system and one or more application programs processing and/or outputting the biometric data for the monitoring system 100. An application program can include software components in the form of computer executable program instructions that cause the CPU 202 to perform some or all of the operations and methods described herein.

The hardware configuration 200 can optionally include a storage device 208 in the form of any suitable non-transitory computer readable medium, such as a hard disc drive, a memory device, a flash drive or an optical drive. The storage device 208, when present, can provide additional memory when high processing requirements exist. The storage device 208 can also store any form of data whether relating to or not relating to biometric data.

The hardware configuration 200 can include one or more input devices 210, such as a keyboard, a numerical keypad, a mouse, a microphone, a touch screen, a sensor, or a gesture-sensitive input device. Through the input device 210, data can be input from the user or another device. For example, a gesture-sensitive input device can receive different gestures to switch between different display modes (e.g., heart rate, weight, ECG, etc.). The input device 210 can also be any other type of input device including an input device not requiring user intervention. For example, the input device 210 can be a communication device such as a wireless receiver operating according to any wireless protocol for receiving signals. The input device 210 can also output signals or data, indicative of the inputs, to the CPU 202 using the bus 206.

The hardware configuration 200 can also include one or more output devices 212. The output device 212 can be any device transmitting a visual, acoustic, or tactile signal to the user, such as a display, a touch screen, a speaker, an earphone, a light-emitting diode (LED) indicator, or a vibration motor. If the output device 212 is a display, for example, it can be a liquid crystal display (LCD), a cathode-ray tube (CRT), or any other output device capable of providing visible output to the user. In some cases, the output device 212 can also function as an input device 210, for example, when a touch screen display is configured to receive touch-based input. The output device 212 can alternatively or additionally be formed of a communication device for transmitting signals. For example, the output device 212 can include the computing device 122 described in association with the monitoring system 100 in FIG. 1.

Although FIG. 2 depicts one hardware configuration 200 that can implement the monitoring system 100, other configurations can be used. The operations of the CPU 202 can be distributed across multiple machines or devices (each machine or device having one or more processors) that can be coupled directly or across a local area or other network. The memory 204 can be distributed across multiple machines or devices such as network-based memory or memory in multiple machines performing operations that can be described herein as being performed using a single computer or computing device for ease of explanation. Although a single bus 206 is depicted, multiple buses can be used. Further, the storage device 208 can be a component of the hardware configuration 200 or can be a shared device that is accessed via a network. Thus, the hardware configuration 200 as depicted in FIG. 2 can be implemented in a wide variety of configurations.

Figure 3:
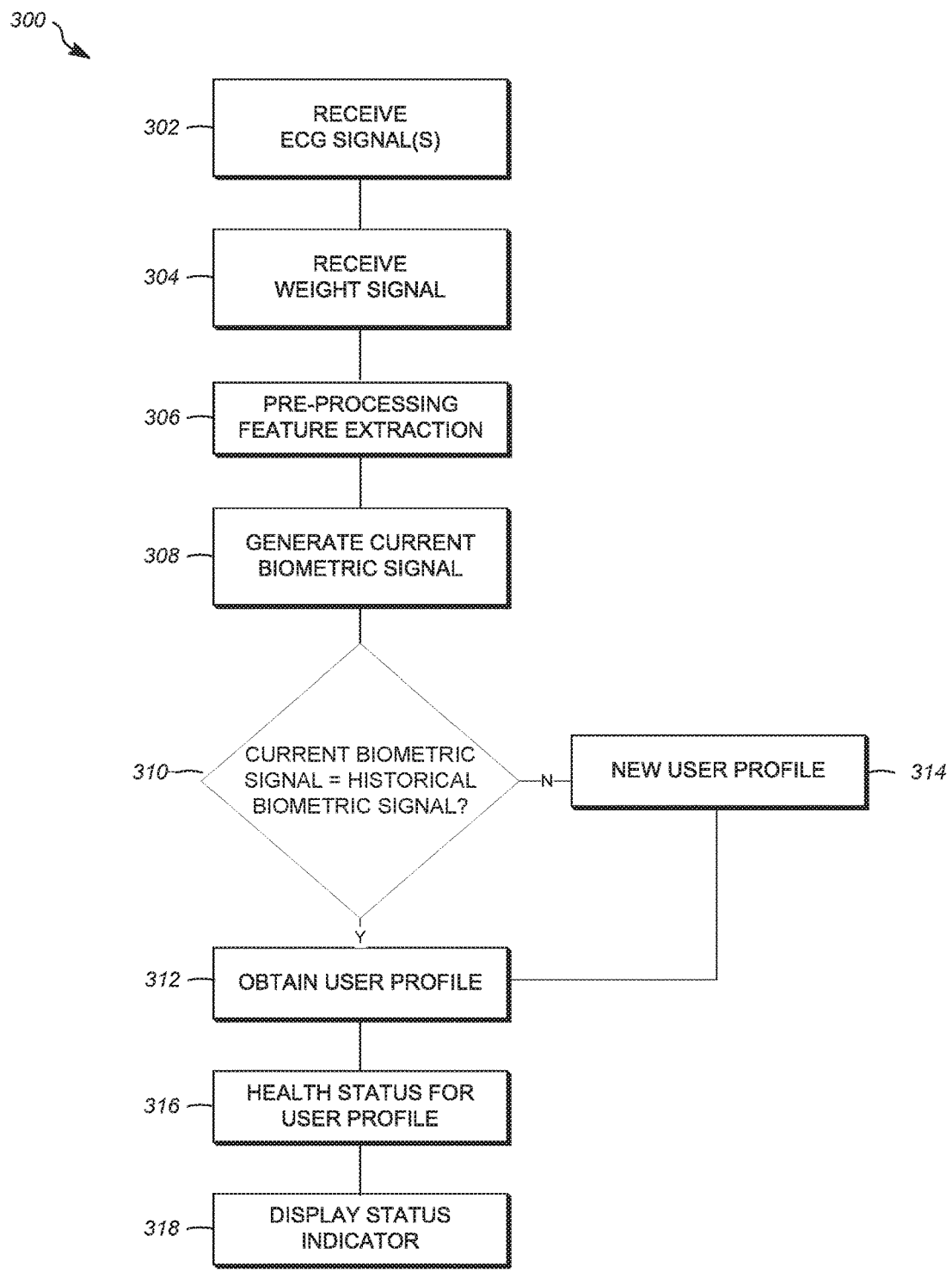
FIG. 3 is a flow chart showing an example of a process overview of biometric signal matching and health status generation.

FIG. 3 is a flow chart showing an example of a method 300 of biometric signal matching and health status generation. The operations described in connection with method 300 can be performed using the monitoring component of the monitoring system 100. The monitoring component can be, for example, the computing device 122, the smart phone 118, the bracelet 120, a remote server (not shown), or the cloud (not shown). The operations described in connection with the method 300 can be embodied as a storage device in the form of a non-transitory computer readable storage medium including program instructions executable by one or more processors that, when executed, cause the one or more processors to perform the operations of the method 300 described below.

At operation 302, one or more ECG signals are received as captured by a combination of the first, second, third, or fourth electrodes 102, 104, 110, 112 of the ECG component based on the user gripping the handle 106 and/or standing barefoot on the platform 114 of the monitoring system 100. At operation 304, a weight signal is received as captured by the weight sensor of the scale component based on the user standing on the platform 114 of the monitoring system 100. Other signals can also be captured by other sensors associated with the monitoring system 100. For example, the user's pulse oxygen level, body temperature, fingerprints, or palm prints can be captured while the user grips the handle 106 and/or stands barefoot on the platform 114.

Both the ECG signals and the weight signals (as well as any other signals captured) typically comprise raw data and need to be processed in order to be properly used to analyze the user's health, for example, to determine disease diagnoses, stress levels, or readiness for exercise. In one implementation, specific ECG signals may be selectively measured based on training provided by the ECG component of the monitoring system 100. At operation 306, the identified ECG and weight signals separately undergo signal pre-processing and feature extraction to determine various features thereof. These processes are described in reference to FIGS. 4 and 5.

Figure 4:
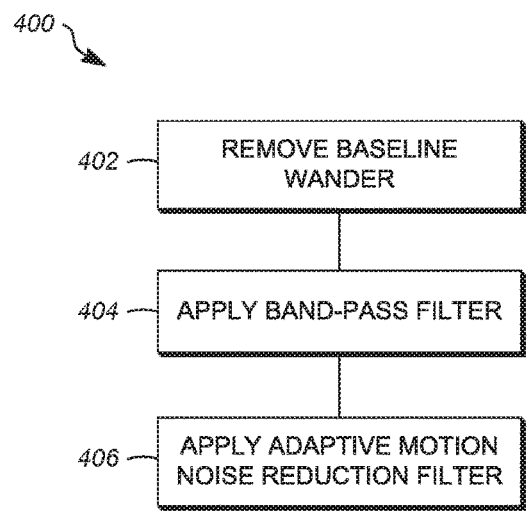
FIG. 4 is a flow chart showing an example of a process of pre-processing biometric signals.

FIG. 4 is a flow chart showing an example of a method 400 for pre-processing each of the ECG and weight signals. At sub-operation 402, a baseline wander, if present, is removed from the ECG and weight signals. At sub-operation 404, a band-pass filter is applied to the ECG and weight signals in order to remove any undesirable data shifts that occurred while the signals were being measured and to reduce the presence of data outside of a range to be observed (e.g., outliers).

An adaptive motion noise reduction filter is applied at sub-operation 406 that filters identified motion noise included within the ECG and weight signals and reduces the motion noise or entirely removes it to better isolate the important data within those signals. Motion noise may include, for example, fluxes and other changes present in the ECG and weight signals due to the user wiggling or otherwise moving in a manner that may interfere with a clear biometric measurement (e.g., where the user's finger moves on second electrode 104 or the user's foot moves on the third electrode 110 while the ECG signals are being measured). The filter adapts to the specific form of the ECG and weight signals.

Figure 5:
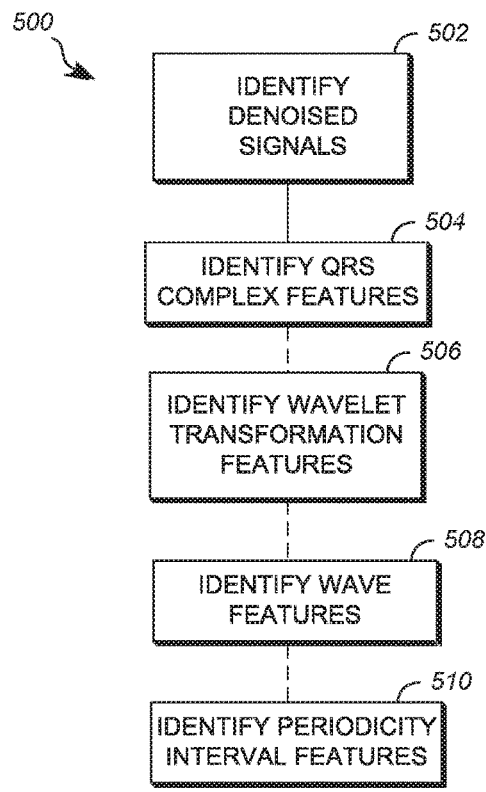
FIG. 5 is a flow chart showing an example of a process of feature extraction for biometric signals.

FIG. 5 is a flow chart showing an example of a method 500 for performing feature extraction on the biometric signals. Initially, at sub-operation 502, the denoised signals are identified, as processed and outputted from the preceding sub-operations 402, 404, and 406 of the method 400. At sub-operation 504, the QRS complex features of the biometric signals are identified to determine the graphical deflections (e.g., wherein Q and S are valleys and R is a peak) representative of the depolarization, for example, of the left and right ventricles of the user's heart. Once the QRS complex features are identified, one or more of three different feature extraction operations may be performed.

At sub-operation 506, the method 500 can be used to identify wavelet transformation features of the denoised biometric signals. At sub-operation 508, other wave features, such as wave magnitude features including various fiducial point features relative to the QRS complex features can be identified. At sub-operation 510, periodicity interval features relative to the QRS complex features and related wave features can be identified. The method 500 can be completed by performing just one of the sub-operations 506, 508, 510, by performing a combination of any two of the sub-operations 506, 508, 510, or by performing all three sub-operations 506, 508, 510.

The above-described wavelet transformation features determined in sub-operation 506 can be identified along with other frequency domain features (including, without limitation, auto-correlation discrete cosine transform features), which may be identified directly from the processed and denoised biometric signals. That is, in one implementation, the wavelet transformation features and other frequency domain features may be identified separately from the temporal domain features of the biometric signals (e.g., wave magnitude features, periodicity interval features, and other fiducial point features), which temporal domain features are identified, for example, based on the identification and detection of the QRS complex features in sub-operation 504.

Notwithstanding the foregoing, it is likely that the most accurate results for the method 300 are obtained by performing all three of the sub-operations 506, 508, 510. In one implementation, the extracted features are normalized after they are identified so that the biometric signals may subsequently be compared based on the same periodicity. The extracted features can be used, for example, to detect a specific disease or fitness condition based on certain rules.

Returning to FIG. 3, at operation 308, an interrelationship between the various features of the pre-processed ECG and weight signals is determined by checking the features against each other. The extracted features of the ECG and weight signals are then merged into a single current biometric signal for further processing and analysis, which will permit the subsequent operations of the method 300 to yield more accurate results than if the operations were performed separately on the various features of the ECG and weight signals.

At decision-tree 310, a multi-modal decision fusion can be used to determine whether the identity of the user currently providing input to the monitoring system 100 is known based on a comparison of the current biometric signal generated during the preceding operations to historical biometric signals associated with existing user profiles. Ideally, biometric characteristics are unique in that no two individuals have identical measurements and are permanent in that the characteristics do not change over time.

However, certain types of biometric characteristics, such as measurements identified via ECG signals, may be insufficient when used alone to determine a user's identity, as the measurements may only identify certain qualities of the characteristic, which may be common in many individuals. By using a combination of ECG signals with weight signals, and optionally, other biometric signals based on the user's body temperature, pulse oxygen level, fingerprints, or palm prints, as provided by the user in the form of a current biometric signal, the identification described herein combines different biometric signals from different sensors to more accurately determine the user's identity.

If the current biometric signal matches a historical biometric signal, for example, by comparing the current biometric signal to historical biometric signals stored with user profiles for the monitoring system 100, the user's identity may be verified, and the method 300 continues to operation 312 where the user's profile is obtained. If the current biometric signal does not match any historical biometric signals, the method 300 continues to operation 314, and a profile generation request soliciting the user to generate a user profile for the monitoring system 100 is sent to the user. Information related to the profile generation request may be displayed to the user, for example, using the display 116, the smart phone 118, or the bracelet 120. The user can respond to the profile generation request by providing information to generate a new profile, which in turn can allow the method 300 to proceed to operation 312 where the new user profile is obtained.

At operation 316, a health status for association with the user profile is determined by machine learning algorithms, such as by classifying the features extracted from the current biometric signal using previously trained disease and fitness models. Disease models allow identification of disease risk factors and/or disease diagnoses for the user based on the current biometric signal. Fitness models allow identification of fatigue levels, stress levels, etc. related to exercise readiness of the user based on the current biometric signal. A more detailed description of how risk factors and disease diagnoses are determined using the current biometric signal is described in reference to FIG. 6.

Figure 6:
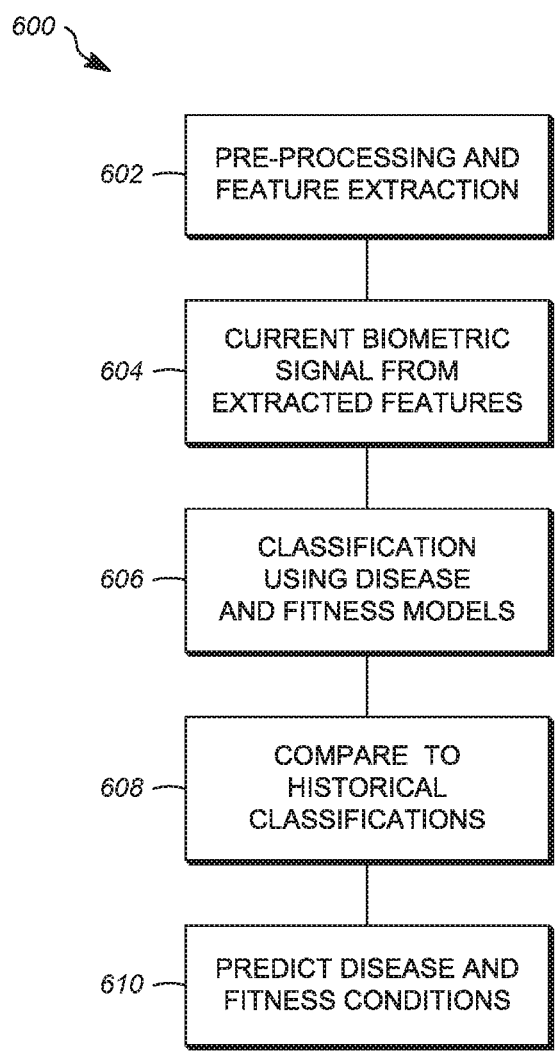
FIG. 6 is a flow chart showing an example of a process of health status determination based on biometric signals.

FIG. 6 is a flow chart showing an example of a method 600 of disease and fitness prediction. At sub-operation 602, pre-processing and feature extraction similar to that described above with respect to FIGS. 4 and 5 may be used to refine the ECG and weight signals prior to classifying the same using disease and fitness models. Different disease and fitness models may be used for the classification. For example, if the user is known to have a disease or fitness condition related to the underlying biometric data, for example, heart disease, obesity, or low heart-rate variability, this information can be used in the subsequent analysis, for example, by analyzing the current biometric signal against historical biometric signals collected from the user.

At sub-operation 604, a current biometric signal is generated using the extracted features of the ECG and weight signals, allowing the subsequent operations of the method 600 to yield more accurate results than if the operations were performed separately on the various features of the ECG and weight signals.

At sub-operation 606, the current biometric signal is classified using disease and fitness models. This classification determines the likelihood of certain diseases or fitness conditions or the presence thereof. For example, the analysis of the current biometric signal may be used to predict and/or diagnosis the user with obesity, high stress, advanced heart age, low heart rate variability, or other medical conditions such as previous heart attack, congestive heart failure, chronic obstructive pulmonary disease (COPD), anemia, lung cancer, asthma, or pneumonia.

At sub-operation 608, the classification can be further supported by determining a health status trend by comparing the classification determined using the current biometric signal to classifications determined using historical biometric signals in order to provide further insight for indicating disease factors, fitness factors, or disease diagnoses for the user. For example, if the user has previously been diagnosed with a relevant disease, fitness condition, or medical condition, the comparison between the current classification and the historical classification can be used to identify the user's treatment progress and other developments in treatment.

Based on the results of the analyses, classifications, and comparisons in sub-operations 606 and 608, an overall prediction of health status for the user, including disease conditions and fitness conditions, can be determined at sub-operation 610. The health status can include information related to the user's weight, heart rate, fatigue level, stress level, heart age, heart rate variability, or heart condition based on classification of the user's current biometric signal, and optionally, the user's historical biometric signals, using various disease models and fitness models.

Returning to FIG. 3, at operation 318, the method 300 includes displaying a status indicator associated with the health status to the user. The status indicator can be shown to the user, for example, using the display 116, the smart phone 118, or the bracelet 120. Other devices can also provide the status indicator to the user. Non-limiting examples of the content represented by the status indicator can include diagnoses or conditions related to the user's weight, heart rate variability, stress level, heart age, or other various heart diseases such as sinus tachycardia, sinus bradycardia, sinus arrhythmia, sinoatrial exit block, atrial fibrillation, atrial flutter, multifocal atrial tachycardia, wandering atrial pacemaker, ectopic atrial rhythms, atrioventricular nodal reentry tachycardia, premature ventricular contractions, ventricular fibrillation, asystole, junctional rhythms, left anterior fascicular block, etc. After operation 318, the method 300 ends.

While the disclosure has been described in connection with certain embodiments and implementations, it is to be understood that the invention is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A method for configuring a monitoring component for a user, comprising:
    receiving an electrocardiograph (ECG) signal of a user from an ECG component;
    receiving a weight signal of the user from a scale component in contact with the user;
    combining features extracted from the ECG signal and the weight signal to generate a current biometric signal, the current biometric signal used to determine an identity of the user;
    responsive to the current biometric signal matching a historical biometric signal stored in a user profile of the user, obtaining the user profile; and
    determining a health status for association with the user profile by classifying the current biometric signal using disease models and fitness models.

2. The method of claim 1, further comprising:
    responsive to the current biometric signal not matching a historical biometric signal, sending a profile generation request soliciting the user to generate a user profile.

3. The method of claim 1, wherein receiving the ECG signal comprises receiving a touch input from the user at two or more electrodes associated with the ECG component.

4. The method of claim 1, wherein the health status is related to the user's weight, heart rate, fatigue level, stress level, heart age, heart rate variability, or heart condition.

5. The method of claim 1, wherein determining the health status further comprises classifying the features extracted from the current biometric signal using previously trained models.

6. The method of claim 1, wherein determining the health status further comprises determining a health status trend by comparing the health status determined using the current biometric signal to a health status determined using the historical biometric signal.

7. The method of claim 1, further comprising:
    displaying, at an output screen associated with the monitoring component, a status indicator associated with the health status.

8. The method of claim 1, wherein the ECG component comprises:
    a first electrode; and
    a second electrode;
        wherein the ECG signal is generated upon user contact with the first and second electrodes.

9. The method of claim 1, wherein the scale component comprises:
    a platform configured to support the user; and
    a weight sensor in communication with the platform and configured to generate the weight signal based on user presence on the platform.

10. A monitoring component, comprising:
    a non-transitory memory; and
    a processor configured to execute instructions stored in the non-transitory memory to:
        receive an electrocardiograph (ECG) signal from an ECG component in contact with a user;
        receive a weight signal from a scale component in contact with the user;
        combine features extracted from the ECG signal and the weight signal to generate a current biometric signal, the current biometric signal used to determine an identity of the user;
        responsive to the current biometric signal matching a historical biometric signal stored in a user profile of the user, obtain the user profile; and
        determine a health status for association with the user profile by classifying the current biometric signal using disease models and fitness models.

11. The apparatus of claim 10, wherein the processor is further configured to:
    responsive to the current biometric signal not matching a historical biometric signal, send a profile generation request soliciting the user to generate a user profile.

12. The apparatus of claim 10, wherein receiving the ECG signal comprises receiving a touch input from the user at two or more electrodes associated with the ECG component.

13. The apparatus of claim 10, wherein the health status is related to the user's weight, heart rate, fatigue level, stress level, heart age, heart rate variability, or heart condition.

14. The apparatus of claim 10, wherein determining the health status further comprises determining a health status trend by comparing the health status determined using the current biometric signal to a health status determined using the historical biometric signal to.

15. The apparatus of claim 10, wherein the processor is further configured to:
    display, at an output screen associated with the monitoring component, a status indicator associated with the health status.

16. A non-transitory computer-readable medium storing a set of instructions for configuring a monitoring component for a user, which when executed by a computer system using a processor become operational with the processor for configurating the monitoring component, the set of instructions comprising instructions to:
    receive an electrocardiograph (ECG) signal from an ECG component in contact with a user;
    receive a weight signal from a scale component in contact with the user;
    combine features extracted from the ECG signal and the weight signal to generate a current biometric signal, the current biometric signal used to determine an identity of the user;

responsive to the current biometric signal matching a historical biometric signal stored in a user profile of the user, obtain the user profile; and determine a health status for association with the user profile by classifying the current biometric signal using disease models and fitness models.

17. The non-transitory computer-readable medium of claim 16, wherein the set of instructions further comprises instructions to:

responsive to the current biometric signal not matching a historical biometric signal, send a profile generation request soliciting the user to generate a user profile.

18. The non-transitory computer-readable medium of claim 16, wherein receiving the ECG signal comprises receiving a touch input from the user at two or more electrodes associated with the ECG component.

19. The non-transitory computer-readable medium of claim 16, wherein the health status is related to the user's weight, heart rate, fatigue level, stress level, heart age, heart rate variability, or heart condition.

20. The non-transitory computer-readable medium of claim 16, wherein determining the health status further comprises determining a health status trend by comparing the health status determined using the current biometric signal to a health status determined using the historical biometric signal to.

21. The non-transitory computer-readable medium of claim 16, wherein the set of instructions further comprises instructions to:

display, at an output screen associated with the monitoring component, a status indicator associated with the health status.

* * * * *